(12) United States Patent
Tice et al.

(10) Patent No.: US 6,432,697 B1
(45) Date of Patent: Aug. 13, 2002

(54) TRANSPARENT SAMPLE CONTAINER

(75) Inventors: Gregory Tice, Lutherville, MD (US); Ming-Hsiung Yeh, New Freedom, PA (US); Thomas M. Gentle, Jr., Red Lion, PA (US); Timothy M. Sullivan, New Freedom, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/496,775

(22) Filed: Feb. 3, 2000

(51) Int. Cl.[7] .............................................. C12M 1/24
(52) U.S. Cl. ........................ 435/288.1; 435/288.7; 435/304.1; 422/82.08; 422/102; 356/246
(58) Field of Search ...................... 435/287.9, 288.1, 435/288.7, 304.1, 808; 422/102, 82.07, 82.08; 356/246

(56) References Cited

U.S. PATENT DOCUMENTS

| | | | |
|---|---|---|---|
| 5,079,144 A | * | 1/1992 | Carr et al. |
| 5,266,486 A | * | 11/1993 | Fraatz et al. |
| 5,567,598 A | * | 10/1996 | Stitt et al. |
| 5,723,189 A | * | 3/1998 | Sudo |
| 5,795,773 A | * | 8/1998 | Read et al. |
| 5,910,287 A | * | 6/1999 | Cassin et al. |
| 6,080,574 A | * | 6/2000 | Berndt |
| 6,164,044 A | * | 12/2000 | Porfano et al. |

FOREIGN PATENT DOCUMENTS

JP          07-53794 A     *   7/1995

* cited by examiner

*Primary Examiner*—William H. Beisner
(74) *Attorney, Agent, or Firm*—Bruce S. Weintraub

(57) ABSTRACT

The present invention relates to a transparent sample container containing, preferably, a liquid bacterial growth media for detecting microbacteria and a process for detecting microbacteria using this sample container. The container is optically transparent, heat resistant, and stable during storage. The container and process provide a bacterial growth medium substantially free of contamination upon prolonged storage of preferably about one year at 40° C.

16 Claims, 1 Drawing Sheet

TRANSPARENT SAMPLE CONTAINER

FIELD OF THE INVENTION

The present invention is directed to a sample container and preferably, to a sample container containing a liquid microorganism growth media, wherein the sample container has good long term stability. More particularly, the present invention is directed to a microbial detecting container that is optically transparent, heat resistant, and resistant to breakage.

BACKGROUND OF THE INVENTION

A vast number of microorganisms are known, many of which are harmful to humans. The presence of these microorganisms creates a continuing need for reliable detection systems and methods of safely and efficiently handling microorganism samples.

In recent years there has been an increased incidence of mycobacterial diseases, and particularly, tuberculosis. To address this increase of such diseases in the population, numerous methods have been introduced for improving the detection of the presence of various mycobacteria, such as, tuberculosis. A number of methods are directed to reducing the time required for accurate detection of the microorganism.

One type of detection system relies on the visual detection of the presence or absence of the growth of microorganisms. Antimicrobic susceptibility tests use this kind of visual detection as an indication of the efficacy of an antimicrobic compound. A disadvantage of this type of test is the time requirements which can require an 18 to 24 day incubation period before sufficient microorganism growth can be detected. An example of this type of method is the Bauer-Kirby Disc Method.

Another method of testing antimicrobic susceptibility uses a plastic panel having several low volume cupulas. Each cupula contains a different test compound or different concentration of a test compound dried on the cupula surface. A test sample containing the suspected microorganism is suspended in a testing medium and an aliquot is delivered to the individual cupulas of the test panel. The dried reagent dissolves and the resulting solution is incubated for sufficient time for the organisms to interact with the reagent and grow. The samples are visually examined for the presence or absence of growth. This method also has the disadvantage of long incubation times thereby preventing a rapid detection.

Light scattering methods have also been developed for determining the susceptibility of microorganisms to antimicrobic compounds. These methods require the use of a light scattering and detection apparatus that are able to detect and measure the changes in size of the microorganism colonies or changes in the number of the microorganism colonies. Information on the antimicrobic susceptibility of various microorganisms have been reported in as little as six hours. However, some microorganisms and antimicrobic compounds can require as long as 18 hours to obtain reliable results.

Another method of determining antimicrobic susceptibility is based on quantifying ATP in the microorganism during incubation by a bioluminescent method. Although this method can produce results in less time than other methods, the method can be difficult to carry out properly to obtain accurate results.

The growth of microorganisms has also been detected by measuring changes in dissolved oxygen. Measuring dissolved oxygen often uses a suitable electrode. However, some of the electrode systems consume oxygen thereby increasing the difficulty of obtaining accurate measurements. Some electrodes require an oxygen permeable membrane to prevent the electrode from interacting with the growth media and the microorganisms. This system still consumes some oxygen and requires time for the solution to equilibrate with the electrodes.

Various methods for optical detection of changes in oxygen concentration have been developed that do not require the use of electrodes in the test solution. These devices can be based on calorimetric or fluorimetic analysis based on changes in the oxygen content of the solutions. These optical processes can be performed economically and in a reasonable time period. One example of a process for detecting microorganisms by detecting changes in oxygen levels is disclosed in U.S. Pat. No. 5,567,598 to Stitt et al. The process disclosed in this patent detects and evaluates the metabolic activity of microorganisms using a fluorescent compound.

Many of these methods require the use of a container or sample tube to contain the sample during the analysis. Glass is a common material for the sample tubes since glass is typically non-reactive with the samples or the instrumentation. A disadvantage of glass tubes is the risk of contamination or exposure to pathogens in the event of breakage. Most non-breakable tubes are not suitable for autoclaving and for use in optical detection systems since the container material interferes with the detection system. Accordingly, there is a continuing need in the industry for improved sample tubes.

SUMMARY OF THE INVENTION

The present invention is directed to a sample container suitable for use in an optical detection system. More particularly, the invention is directed to a sample container made from a cyclic olefin copolymer. The invention is further directed to a method of detecting organisms using the sample container.

Accordingly, a primary object of the invention is to provide a sample container for detecting the presence of microorganisms by fluorescence analysis.

Another object of the invention is to provide a non-breakable sample container produced from a cyclic olefin copolymer that is optically clear to allow visual detection of a fluorescent compound by ultraviolet light and visual inspection of a microorganism growth medium.

A further object of the invention is to provide a sample container made from a cyclic olefin copolymer that is heat resistant to at least 250° C. without distortion or hazing of the container.

A still further object of the invention is to provide a sample container made from a cyclic olefin copolymer that is able to withstand an internal pressure of about 25 psi without rupturing or distortion.

Another object of the invention is to provide a sample container made from a cyclic olefin copolymer that is non-reactive with a liquid microorganism growth media and provides a shelf stable environment for a microorganism growth media for extended periods of time.

These and other objects of the invention are basically attained by providing a sample container assembly comprising a container having a side wall, a bottom wall, an open top end, and a liquid sample contained therein, the container being formed from a cyclic olefin copolymer having a transparency sufficient to visually observe turbidity in said sample; and a closure coupled to the open end of the container, wherein the sample is substantially free of contamination upon prolonged storage of preferably about one year at 40° C.

The objects of the invention are further attained by providing a microbial detecting container assembly comprising a transparent container having a side wall, a bottom wall and an open top end, a fluorescent sensor compound that exhibits a reduction in fluorescent intensity when exposed to oxygen, and a microorganism growth media contained within the container, the container being made by a molding process from a cyclic olefin copolymer, wherein the container has a transparency sufficient to visually detect turbidity in the microorganism growth media, and wherein the microorganism growth medium is substantially free of contamination after storage for, preferably, at least about 1 year at about 40° C.; and a closure coupled to the open end of the container.

The objects of the invention are also attained by providing a method of detecting the presence of microorganisms in a sample comprising providing a transparent container having a sidewall, a bottom wall, an open top end, and a closure coupled to the open top end, the container containing a microorganism growth medium, wherein the container is made by a molding process from a cyclic olefin copolymer, the container having a transparency sufficient to visually detect turbidity in said bacterial growth media and said bacterial growth medium being substantially free of contamination after storage for, preferably, at least about 1 year at 40° C., adding a sample to said transparent container, irradiating said fluorescent sensor with a light source capable of fluorescing said fluorescent sensor, detecting fluorescent light intensity from said fluorescent sensor while irradiating said fluorescent sensor, and comparing said detected fluorescent light intensity with a control and determining the presence of microorganisms in the sample.

The objects advantages and other salient features of the invention will become apparent from the following detailed description of the invention which taken in conjunction with the annexed drawings disclose various embodiments of the invention.

BRIEF DESCRIPTION OF THE DRAWINGS

The following is a brief description of the drawings in which.

DETAILED DESCRIPTION OF THE INVENTION

The present invention is directed to a container and to a method of using the container for detecting the presence of microorganisms. More particularly, the invention is directed to a microbial detecting container and to a method of detecting the presence of microorganisms in a sample within the container.

Figure 1:
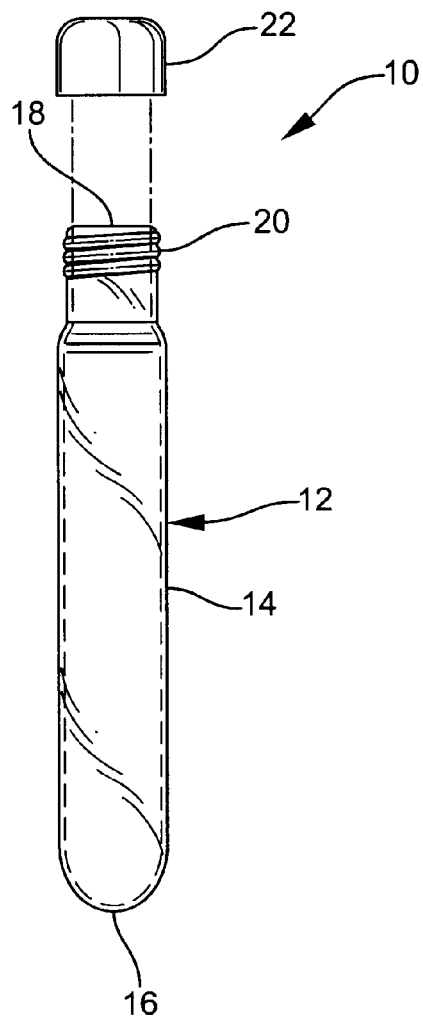
FIG. 1 is an exploded side elevational view of the container in a preferred embodiment of the invention.

The container of the present invention can be a number of shapes and sizes depending on the type of sample being tested and the instrumentation used for the sample analysis. In one preferred embodiment shown in FIGS. 1 and 2, the container 10 includes a tube 12 having a generally cylindrical side wall 14 with a closed, rounded bottom 16. The tube 12 has an open top end 18 with external threads 20. A cap 22 having internal threads is provided for coupling with the threads 20 of the tube 12 and forming a tight seal to prevent leakage of the contents. In one embodiment of the invention the tube has a capacity of about 12.0 ml with a length of about 10 cm and width of about 1.5 cm. In further embodiments, the shape and dimensions of the container can vary depending on the specific requirements of the analyzing procedure.

Figure 2:
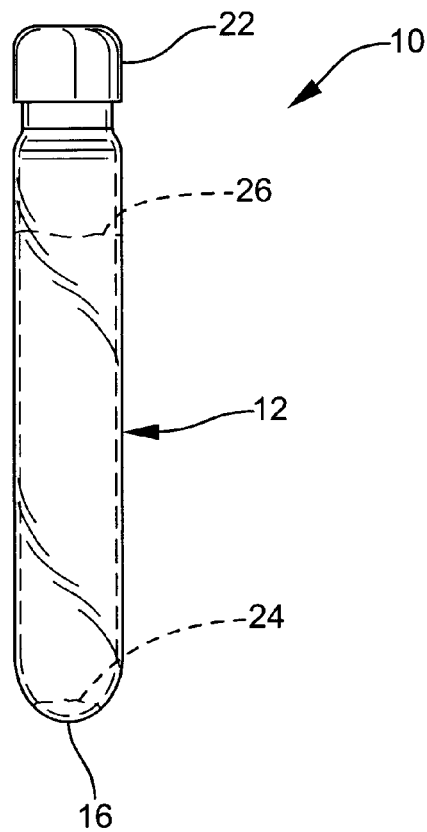
FIG. 2 is a side elevational view of the container of FIG. 1 showing a fluorescent detection compound and a microorganism growth media solution contained therein.

The container of the invention in a preferred embodiment is a sample tube for the detection of microorganisms by various methods, and particularly by fluorescent measurements. For this purpose, the tube 12 as shown in FIG. 2 includes a detecting compound 24, such as a fluorescing compound, in the bottom wall 16. A microorganism nutrient growth media 26 is provided in the tube to support the growth of the microorganism being detected.

The tube 14 is used for detecting the presence or absence of various microorganisms, many of which are pathogenic. In one embodiment, the tube is used for detecting the presence of tuberculosis in a test sample. Therefore, the tube 14 is made from a non-breakable or fracture resistant polymeric material to minimize the risk of breakage and to reduce the risk of exposing the user to toxins or pathogens in the sample. It has been found that a tube made from a cyclic olefin copolymer has sufficient strength to resist breaking when dropped during normal use of the tube.

The container of the invention is required to be optically transparent or substantially transparent to allow visual inspection of the growth media contained therein. The container and growth media are required to be shelf stable for extended periods of time, typically up to about one year. In preferred embodiments, the container is non-reactive with the growth media so that the growth media is free of suspended solids or other contaminants from the container after storage of about one year at about 40° C. Turbidity of the growth medium is determined visually through the transparent tube so that it is important to retain the transparency throughout the storage life of the tube.

The sample tube is produced by molding the cyclic olefin copolymer using known molding processes depending on the desired shape and dimension of the sample tube. In one embodiment, the sample tube is made by an injection molding process. Alternatively, the sample tube can be made by an injection blow molding process.

After the tube is molded, a fluorescent detecting compound is placed in the bottom of the container and the container is filled with a microorganism growth media. Typically the tube is cleaned and sterilized before the fluorescent detecting compound and the growth media are placed in the tube. After filling the tube with the microorganism growth media, the tube is closed by the threaded cap or other closure and autoclaved for sufficient time to sterilize the tube. During autoclaving, the tube is heated thereby causing an increase in the internal pressure of the tube. In preferred embodiments, the sample tube with the microorganism growth media is able to undergo autoclaving at least at about 250° F. and is able to withstand an internal pressure of at least 25 psi without rupturing, hazing, increasing brittleness of the tube, or contamination of the growth media by the tube material. In one embodiment, the sample tube is sterilized by steam autoclaving. After autoclaving, the microorganism growth media stored in a cyclic olefin polymer container is stable for at least one year and shows no turbidity or solid matter by visual inspection.

In preferred embodiments, the container is made from a cyclic olefin copolymer. These copolymers are thermoplastics suitable for injection molding or injection blow molding. The cyclic olefin copolymers have been found to have high transparency, good water vapor barrier properties and heat resistance properties for use in producing the sample tubes for the fluorescence detection of microorganisms.

The cyclic olefin copolymers are block copolymers of a cyclic olefin and ethylene having the formula

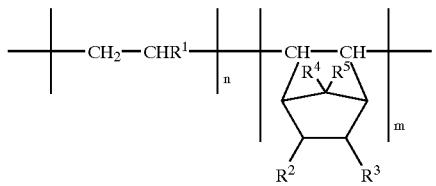

where $R^1$, $R^2$, $R^3$, $R^4$ and $R^5$ are the same or different and are selected from the group consisting of hydrogen and a $C_1$–$C_8$ alkyl radical, and n and m are integers. In a preferred embodiment $R^4$ and $R^5$ are hydrogen.

Particularly preferred cyclic olefin copolymers are produced from a cyclic olefin and an acyclic olefin. Examples of preferred cyclic olefin copolymers are available under the trade name Topas (Thermoplastic Olefin Polymer of Amorphous Structure) from Hoechst Celanese of Summit, N.J. One preferred cyclic olefin copolymer is sold under the trade name Topas-6015 having a light transmission of 92% determined by ASTM D-1003. Other suitable commercially available cyclic olefin copolymers are available under the trade names Topas-8007, Topas-5013 and Topas-6017. In one embodiment of the invention, the sample tube is made from Topas-6015 by an injection blow molding process. The resin granules are dusted with an anti-blocking agent, such as Hoechstwax C sold by Hoechst Celanese of Summit, N.J. The granules are dusted by tumbling the additive in the form of a fine powder to cause the additive to adhere to the resin granules. The resulting mixture is then fed into the screw of an extruder of the molding machine in the usual manner. The additive and the base resin are thoroughly mixed in passing through the extruder and reach the mold in the mixed state.

The cyclic olefin copolymers can be produced by various processes as known in the art. For example, suitable cyclic olefin copolymers can be produced by polymerizing about 0.1 to 100% by weight of a monomer having the formula

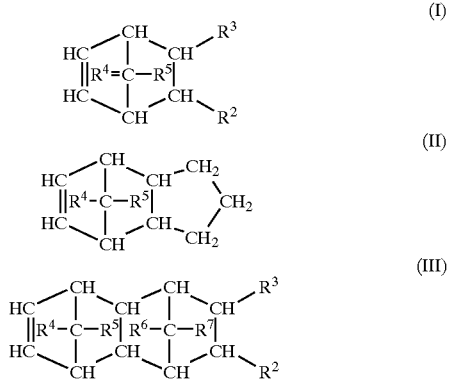

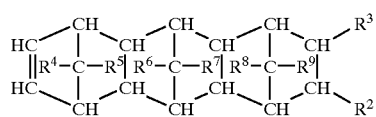

where $R^2$ and $R^9$ are the same or different and are selected from the group consisting of hydrogen and a $C_1$–$C_8$ alkyl; up to 99.9% by weight of a cyclic olefin having the formula

where n is an integer from 2 to 10; and up to 99.9% by weight of an acyclic olefin having the formula

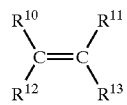

wherein $R^{10}$–$R^{13}$ are the same or different and selected from the group consisting of hydrogen and $C_1$–$C_8$ alkyl. In the above formulas, the alkyl can be linear or branched.

The monomers are polymerized by a metallocene compound of group IVb to Vb and an aluminoxane. Examples of processes for synthesizing the cyclic olefin copolymers are disclosed in U.S. Pat. Nos. 5,087,677, 5,331,057, 5,324,801 and 5,422,409, which are hereby incorporated by reference in their entirety.

Suitable cyclic olefin monomers for producing the copolymers include, for example, norborene, tetracyclododecene, bicyclo[2,2,1]hept-2-ene, 1-methylbicyclo[2,2,1]hept-2-ene, and hexacyclo-4-heptadene. The preferred cyclic olefin can be copolymerized with an acyclic monomer, such as, ethylene, propylene, butylene or mixtures thereof. The cyclic olefin copolymers available under the trade name Topas are copolymers of norbene and ethylene.

The copolymers can be blended with various additives, such as antistatic agents, neutralizing agents, antioxidants, and organic peroxides as known in the art to improve the processing properties and enhance the qualities of the finished product. Suitable antioxidants include phenolic antioxidants, phosphate antioxidants and organic phosphite antioxidants. Typical neutralizing agents include stearic acid salts, oxides and hydroxides of alkaline earth metal.

The container of the invention is particularly suitable for a sample container used in a method of measuring and detecting aerobic microorganisms by visually observing fluorescence of the sample. To ensure accurate results from the detection process, the sample tube must retain its transparency after autoclaving and storage for prolonged periods of time.

The fluorescent compound is a compound that is quenched at oxygen concentrations normally found in a microorganism growth media, which is typically a dissolved oxygen concentration in equilibrium with a headspace oxygen concentration of about 7% to about 21%. Suitable fluorescent compounds include tris-2,2'bipyridyl ruthenium (II) salts such as the chloride salt Ru(DPP)$_3$Cl$_2$ and 9,10-diphenyl anthracene (DPA). The fluorescent compounds can be applied directly to the inner surfaces of the sample tube as a coating or combined within a suitable matrix that is applied to at least a portion of the inner surface of the sample tube. In a preferred embodiment the invention, the fluorescent compound is dispersed throughout a silicone rubber that is permeable to oxygen. The silicone rubber is applied to the bottom of the sample tube and cured. Preferably the fluorescent compound exhibits little or no fluorescence in the presence of oxygen.

A suitable microorganism growth medium is placed in the sample tube and the tube is sealed by a suitable closure. The microorganism growth medium can be selected depending on the microorganism being detected. A typical growth medium can be a broth of, for example, Mueller Hinton II (BD Microbiology Systems), Brucella and Middlebrook 7H9 as known in the art. Typically, the sample tube contains about 4.0 ml to about 7.0 ml of the microorganism growth media. The microorganism does not fill the sample tube in preferred embodiments so a head space is present above the growth medium.

A sample suspected of containing a microorganism is added to the sample container and the cap secured to the sample container to isolate the interior from atmospheric oxygen. In alternative embodiments, the sample container can be left open to the atmosphere. The sample container is then incubated for sufficient period of time at a suitable incubating temperature for the specific microorganism being detected. Thereafter the sample container is irradiated from a fluorescent light source, typically ultraviolet light, and the fluorescence of the fluorescent compound detected. The intensity of the fluorescence is compared with a control to determine the presence of a microorganism. An example of this method is disclosed in U.S. Pat. No. 5,567,598, which is hereby incorporated by reference.

The fluorescence of the compound in the sample tube can be detected and measured using an automated testing apparatus. For example, the samples can be analyzed using the detecting system sold under the trademark BACTEC MGIT 960 for mycobacteria testing by Becton Dickinson Microbiology Systems, Sparks, Md. Alternatively, the fluorescent emissions can be measured and detected using a Perkin-Elmer LS-SB equipped with a microtiter reader. In still further embodiments, the ultraviolet light source can be a hand held unit and the fluorescence observed visually. The wavelength of the ultraviolet light can be selected depending on the particular fluorescent compound.

The process of the invention is particularly suitable for detecting the presence of a variety of microorganisms and particularly mycobacteria. The sample container made from the cyclic olefin copolymer maintains its transparency throughout the storage period and is sufficiently transparent to provide accurate fluorescence measurement data. The cyclic olefin copolymers can be steam autoclaved without increasing the brittleness of the sample tube or affecting the gas and water barrier properties. The cyclic olefin copolymers have a slight yellow color with very low haze that does not interfere with fluorescent measurements or visual detecting of tubitity of the growth media.

While various embodiments of the invention have been selected to show the invention, it will be understood by those skilled in the art that various modifications and changes can be made without departing from the scope of the invention.

What is claimed is:

1. A sample container assembly comprising:
    a container having a side wall, a bottom wall, an open top end, and a liquid sample contained therein, said container being formed from a cyclic olefin copolymer having a transparency sufficient to visually observe turbidity in said sample, and wherein said container is resistant to heating at a temperature of at least 250° C. and said container has a wall thickness sufficient to withstand an internal pressure of at least 25 psi; and
    a closure coupled to said open end of said container, wherein said sample is substantially free of contamination after storage in said assembly for an extended period of time under ambient conditions.

2. The sample container assembly of claim 1, wherein said extended period of time under ambient conditions is at least about one year at about 40° C.

3. The sample container assembly of claim 1, wherein said sample is a microorganism growth medium.

4. The sample container assembly of claim 1, further comprising a fluorescent sensor compound fixed to an inner surface of said container that when exposed to oxygen exhibits a reduction in fluorescent intensity upon exposure to a fluorescing light.

5. The sample container assembly of claim 4, wherein said container is substantially transparent to said fluorescing light.

6. The sample container of claim 4, wherein said fluorescent sensor compound comprises at least one compound selected from the group consisting of tris-4,7-diphenyl-1,10-phenanthroline ruthenium (II) salts, tris-2,2'-bipyridyl ruthenium (II) salts, 9,10-diphenyl anthracene, and mixtures thereof.

7. The sample container of claim 6, wherein said fluorescent sensor compound is tris-4,7-diphenyl-1,10-phenanthroline ruthenium (II) chloride.

8. The sample container of claim 6, wherein said fluorescent sensor compound is tris-2,2'-bipyridyl ruthenium (II) chloride hexahydrate.

9. The sample container of claim 1 wherein said cyclic olefin copolymer is a copolymer of a cyclic olefin and ethylene.

10. The sample container of claim 1 wherein said cyclic olefin copolymer has the formula

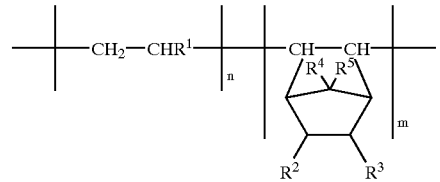

where n and m are integers, $R^1$–$R^5$ are the same or different and are selected from the group consisting of a hydrogen atom and a $C_1$–$C_8$ alkyl radical.

11. A microbial detecting container assembly comprising a transparent container having a side wall, a bottom wall and an open top end, a fluorescent sensor compound that exhibits a reduction in fluorescent intensity when exposed to oxygen, and a microorganism growth medium contained within said container, said container being made by a molding process from a cyclic olefin copolymer, wherein said container has a transparency sufficient to visually detect turbidity in said microorganism growth medium, wherein said container is resistant to heating at a temperature of at least 250° C. and said container has a wall thickness sufficient to withstand an internal pressure of at least 25 psi and wherein said microorganism growth media is substantially free of contamination after storage of at least about 1 year at about 40° C.; and
a closure coupled to said open end of said container.

12. The microbial detecting container of claim 11, wherein said fluorescent sensor compound comprises at least one compound selected from the group consisting of tris-4,7-diphenyl-1,10-phenanthroline ruthenium (II) salts, tris-2,2'-bipyridyl ruthenium (II) salts, 9,10-diphenyl anthracene, and mixtures thereof.

13. The microbial detecting container of claim 11, wherein said fluorescent sensor compound is tris-4,7-diphenyl-1,10-phenanthroline ruthenium (II) chloride.

14. The microbial detecting container of claim 11, wherein said fluorescent sensor compound is tris-2,2'-bipyridyl ruthenium (II) chloride hexahydrate.

15. The microbial detecting container of claim 11, wherein said cyclic olefin copolymer is a copolymer of a cyclic olefin and ethylene.

16. The microbial detecting container of claim 11, wherein said cyclic olefin copolymer has the formula

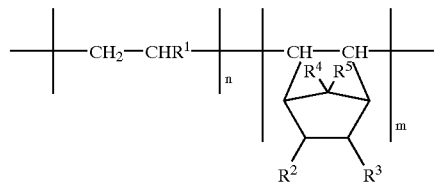

where n and m are integers, $R^1$–$R^5$ are the same or different and are selected from the group consisting of a hydrogen atom and a $C_1$–$C_8$ alkyl radical.

* * * * *